United States Patent [19]

Nixon et al.

[11] Patent Number: 4,723,545
[45] Date of Patent: Feb. 9, 1988

[54] POWER ASSISTED ARTHROSCOPIC SURGICAL DEVICE

[75] Inventors: James E. Nixon, Philadelphia, Pa.; Bruno Mombrinie, Voorhees, N.J.

[73] Assignee: Graduate Hospital Foundation Research Corporation, Philadelphia, Pa.

[21] Appl. No.: 825,412

[22] Filed: Feb. 3, 1986

[51] Int. Cl.⁴ .............................................. A61F 17/32
[52] U.S. Cl. ..................... 128/305; 128/755
[58] Field of Search ............. 128/305, 318, 749, 310, 128/751, 750, 754, 752, 755; 604/22; 30/272 A, 272 R, 169, 208, 215

[56] References Cited

U.S. PATENT DOCUMENTS

| | | | |
|---|---|---|---|
| 2,262,315 | 11/1941 | Davies | 30/208 |
| 3,712,386 | 1/1973 | Peters | 128/305 |
| 3,730,185 | 5/1973 | Cook et al. | 128/305 |
| 3,734,099 | 5/1973 | Bender et al. | 128/305 |
| 4,088,369 | 5/1978 | Prater | 30/272 R |
| 4,200,106 | 4/1980 | Douvas et al. | 128/305 |
| 4,203,444 | 5/1980 | Bonnell et al. | 128/276 |
| 4,215,475 | 8/1980 | Morford et al. | 30/272 A |
| 4,258,716 | 3/1981 | Sutherland | 128/318 |
| 4,444,184 | 4/1984 | Oretorp | 128/305 |
| 4,576,164 | 3/1986 | Richeson | 128/305 |
| 4,601,290 | 7/1986 | Effron et al. | 128/305 |
| 4,601,710 | 7/1986 | Moll | 128/305 |
| 4,643,190 | 2/1987 | Heimberger | 128/305 |

Primary Examiner—C. Fred Rosenbaum
Assistant Examiner—Mario Costantino
Attorney, Agent, or Firm—Caesar, Rivise, Bernstein, Cohen & Pokotilow, Ltd.

[57] ABSTRACT

A surgical instrument, particularly suited for arthroscopic surgery, for cutting tissue located at an interior site within the body of a patient. The instrument includes a body or handle portion from which an elongated stem extends. A blade is located at the free end of the stem. The blade includes a generally elongated cutting edge portion which extends generally parallel to the longitudinal axis of the instrument. Motor means is provided within the body portion for effecting the oscillation (reciprocal pivoting) of the cutting edge portion with respect to the body portion about the longitudinal axis through a small arc, e.g. 20°-25°. A retractable/extendable shroud (sheath) is provided to cover the blade and stem to enable the blade end of the instrument to be readily inserted into the body of the patient through a small opening while preventing exposure of any surrounding tissue to the blade. The shroud is retractable to expose the blade when cutting is desired. The cutting operation is effected by bringing the cutting edge portion into contact with the material to be cut while moving the edge portion therethrough as the blade is oscillated.

21 Claims, 10 Drawing Figures

FIG. 2

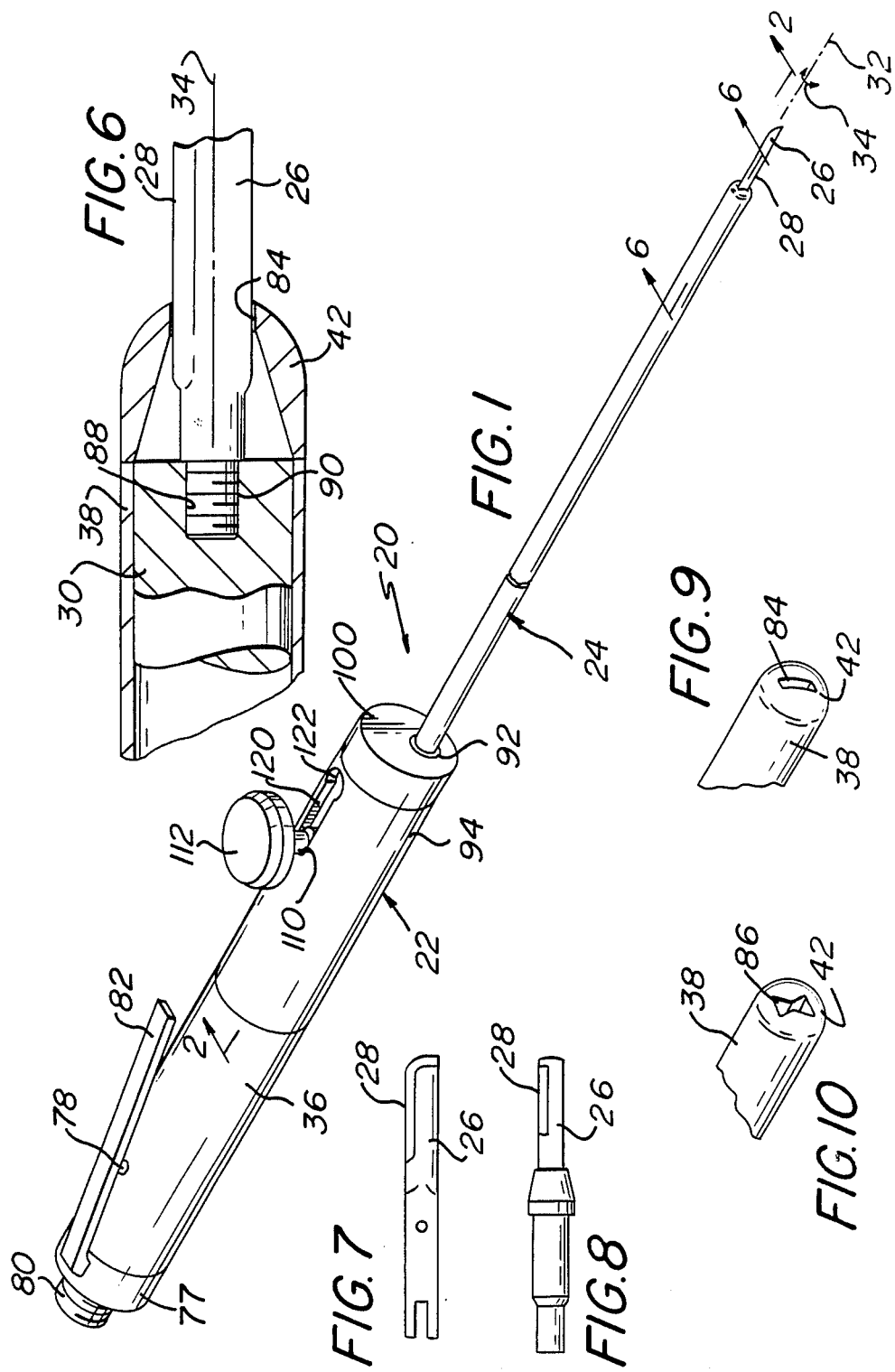

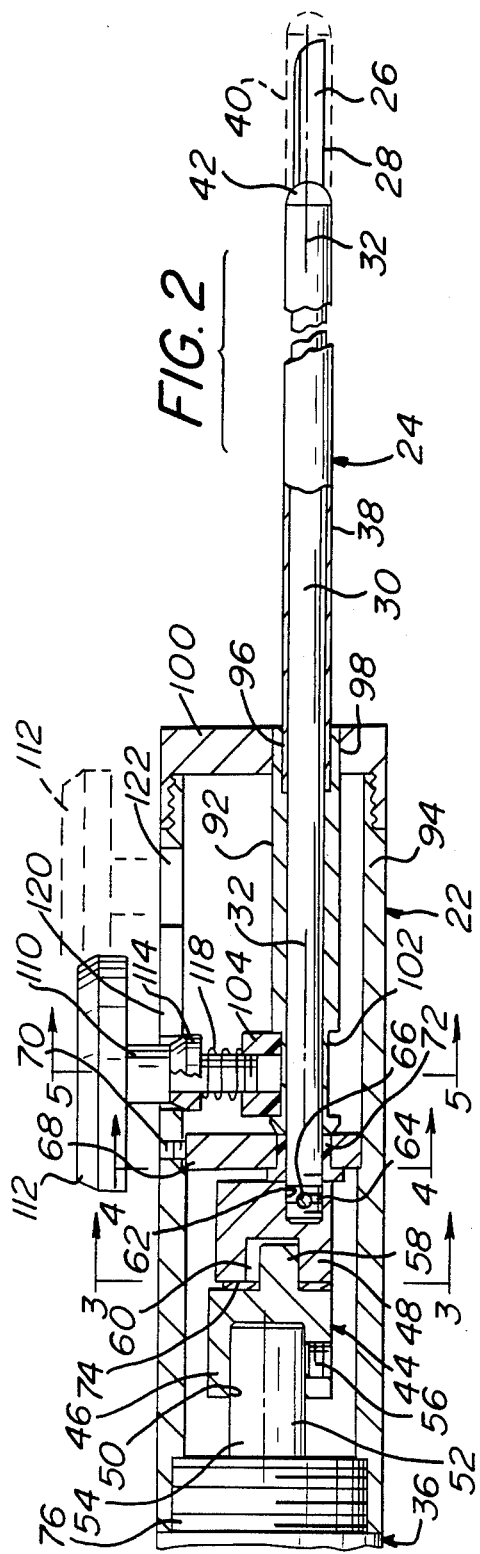
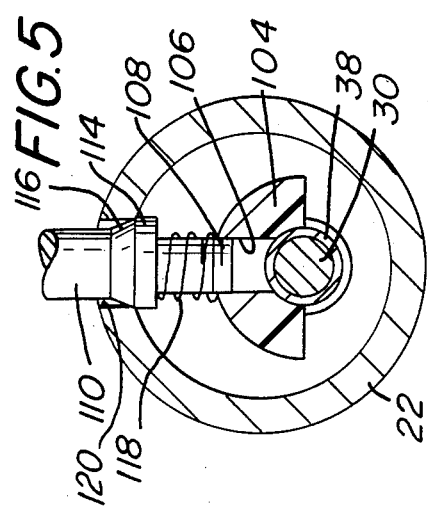
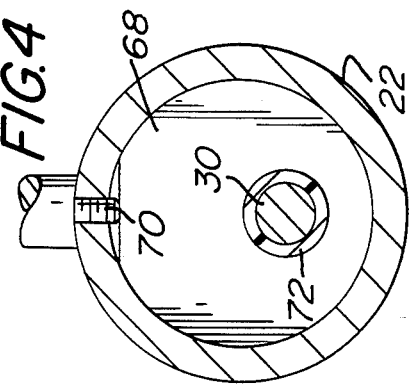
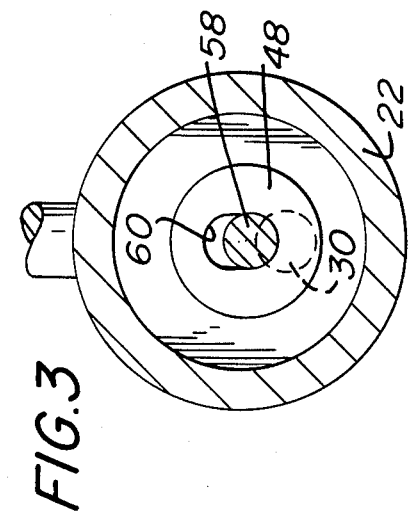

POWER ASSISTED ARTHROSCOPIC SURGICAL DEVICE

BACKGROUND OF THE INVENTION

This invention relates generally to cutting devices and more particularly to surgical instruments for use in applications requiring limited access and/or careful instrument manipulation, such as arthroscopic surgery.

With the increase of active participations of Americans in fitness and exercise related activities has come a concomitant increase in sports/exercise related injuries, particularly to the joints. Such injuries frequently require surgery for correction. One common type of procedure now in use for intra-articular (joint) surgery is arthroscopic surgery. Such surgery involves viewing and surgical instruments probes inserted into the joint region through a small opening and without laying the joint open. Some of the more common procedures done arthroscopically are accomplished on the knee and include removal of loose bodies, shaving of the patella, resection of cartilage, resection of the meniscus, removal of synovial tissue, realignment of the knee cap, and abrasion of exposed areas of bone to promote regrowth of cartilage. Other areas of the body, such as the ankle, elbow, hip, and wrist, are also being arthroscopically repaired.

Various manual (hand) or powered instruments are commercially available for effecting arthroscopic surgery. Examples of hand instruments are forceps, grasps, knives, punches, etc. Powered instruments frequently make use of rotating blades for effecting a shaving-like procedure on joint tissue. For example, in U.S. Pat. No. 4,203,444 there is shown a shaver-type powered arthroscopic surgical instrument.

Unfortunately, current methods for resecting cartilage using hand or manual instruments during arthroscopic surgery have limitations. In this regard during arthroscopic surgery the hand-to-eye motor coordination of the surgeon is frequently impaired due to the fact that the surgeon carries out the procedure by watching an image on a monitor and not looking directly at the situs of the surgery. In addition, the surgeon usually holds the arthroscope in one hand, a knife or punch in the other, and uses them concomitantly. Due to the toughness or cut-resistence of the tissues cutting requires considerable pressure, with some constraints on flexibility. Moreover, reshaping of tissues is difficult since the use of a knife or a punch does not provide a smooth surface. The use of powered instruments has not obviated all of the problems of the prior art. For example the shaver-type devices while well suited to shave cartilage have proven too slow for resection.

Thus, the need exists for a surgical instrument which facilitates resection and molding of cartilage surface quickly, with little need for hand pressure, thus maximizing flexibility of movement in all directions, and while not obscuring vision of the surgeon.

OBJECTS OF THE INVENTION

Accordingly, it is a general object of the instant invention to provide a cutting instrument or device which overcomes the disadvantages of the prior art.

It is a further object of the instant invention to provide a surgical device for effectively cutting or shaping of tissue in surgical applications affording limited access to the surgical situs.

It is a further object of the instant invention to provide a surgical device which is simple in construction and effective in operation.

It is a further object of the instant invention to provide a surgical instrument having a cutting blade which can be readily inserted into the body of the patient through a small opening and without the danger of damage to surrounding tissue during the insertion process.

It is a further object of this invention to provide a surgical device which has particular utility for arthroscopic surgical procedures.

SUMMARY OF THE INVENTION

These and other objects of the instant invention are achieved by providing a device for cutting material. The device basically comprises a body portion adapted to be held, a blade portion having an elongated cutting edge portion, and means for mounting the blade with respect to the body portion so that the cutting edge portion extends generally parallel to the longitudinal axis. The blade is mounted so that its cutting edge portion can oscillate with respect to the body portion about the longitudinal axis through a small arc. This action ensures that when the cutting edge portion is brought into contact with the material to be cut and is moved therethrough while that edge portion is oscillated the material is cut efficiently.

In one aspect of the invention the means for mounting the cutting blade comprises an elongated stem having a free end portion to which the blade is secured. The stem is of small diameter to enable the blade to be inserted through a small opening in the body of the patient to a site at which cutting is to be effected.

In accordance with another aspect of the invention the device includes cover means for covering the cutting edge portion to enable the instrument to be inserted into the body of a patient without any danger of surrounding tissue being cut during the insertion process.

DESCRIPTION OF THE DRAWING

Other objects and many of the attendant advantages of the instant invention will be readily appreciated as the same becomes better understood by reference to the following detailed description when considered in connection with the accompanying drawing wherein:

FIG. 1 is a perspective view of a surgical instrument constructed in accordance with this invention;

FIG. 2 is an enlarged, sectional view taken along line 2—2 of FIG. 1;

FIG. 3 is an enlarged, sectional view taken along line 3—3 of FIG. 2;

FIG. 4 is an enlarged, sectional view taken along line 4—4 of FIG. 2;

FIG. 5 is an enlarged, sectional view taken along line 5—5 of FIG. 2;

FIG. 6 is an enlarged, side elevational view, partially in section, showing the free end of the instrument shown in FIG. 1 when arranged for cutting;

FIG. 7 is a plan view of a conventional surgical blade which can be used with this invention;

FIG. 8 is a plan view of an alternative conventional surgical blade which can be used with this invention;

FIG. 9 is a perspective view of one embodiment of the free end of the instrument shown in FIG. 1; and FIG. 10 is a view similar to that of FIG. 9 but showing an alternative embodiment of the free end of the instrument shown in FIG. 1.

DETAILED DESCRIPTION OF THE PREFERRED EMBODIMENT

Referring now in greater detail to the various figures of the drawing wherein like reference characters refer to like parts, there is shown at 20 in FIG. 1 a surgical instrument constructed in accordance with the subject invention. Before describing the details of that instrument it must be pointed out that while the instrument is particularly suited for effecting surgical procedures, such as arthroscopic surgery or other intra-articular (intra-joint surgery), it can be used for other surgical procedures as well. Moreover, the subject invention can even be used for non-surgical applications wherein cutting of tough and cut resistent material is desired, such as the cutting of leather.

The surgical instrument 20 basically comprises a housing assembly 22, an elongated stem/shroud assembly 24, and a cutting blade 26. The cutting blade can be of any construction, such as a conventional "Brimfield" blade (FIG. 1), a "Stille" blade (FIG. 7), a "Beaver" blade (FIG. 8), or any other conventional or non-conventional blade having an elongated cutting edge 28 (FIGS. 2 and 6). Moreover, the cutting edge 28 need not be linear and thus can be curved, notched, etc., depending on the surgical application.

As shown clearly in FIG. 2 the stem/shroud assembly includes a stem member 30 (FIG. 2). This member serves as the mount for the blade 26 on the housing assembly 24 but with the blade spaced a substantial distance from the housing assembly. The details of the stem 30 will be described later. Suffice now to state that member 30 is an elongated element extending along a longitudinal axis 32 of the instrument 20 and is of sufficiently small diameter to enable it to be inserted into the body of the patient through a small opening or puncture, such as provided during arthroscopic surgical procedures. In addition to mounting the blade, the stem 30 also serves as a component of means, to be described later, for causing the blade to be reciprocally pivoted (i.e., oscillated) through a small arc 34, e.g., at least 15°-30°, and preferably 20°-25°, about the longitudinal axis 32 under power provided from a motor 36 mounted to the rear of the housing assembly.

The shroud/stem assembly 24 also comprises an elongated tubular sheath or shroud 38 which covers the stem 30 and is arranged to slide therealong between either an extended position, shown by the phantom line 40 in FIG. 2 wherein the shroud completely covers or shields the blade 26, and a retracted or solid line position, shown in FIG. 2, wherein the blade 26 is exposed. In the extended position with the blade covered, the instrument 20 can be inserted through a small opening or puncture in the body of the patient so that it is located at the desired situs and without exposing any bodily tissue adjacent the opening from being cut by the blade during the insertion process. Once the instrument is at the desired internal location the shroud 38 is retracted, to thereby expose the blade 26 so that the cutting procedure can commence. The means for effecting the retraction/extension of the shroud will be described later.

As can be seen in FIG. 2 the shroud 38 is a thin walled member whose outside diameter is not substantially greater than the outside diameter of the stem 30. Accordingly, the outside diameter of the shroud/stem assembly 24 is of sufficiently small diameter to readily permit its insertion through a small opening or puncture into the body of the patient. In order to facilitate the insertion process, the free end of the shroud 38 is in the form of a domed tip 42 which is secured, such as by silver solder, to the tubular portion of the shroud 38.

As mentioned earlier the instrument 20 operates so that the blade's cutting edge portion 28 is reciprocally swept or pivoted in through a small arc 34 about the longitudinal axis 32. This oscillating action facilitates the cutting process performed by the blade 28 notwithstanding the toughness or cut-resistance of the tissue to be repaired. Thus, it has been found that the device of the subject invention can quickly and easily cut through and/or shape the gristle-like materials forming meniscal cartilage or cut through hard joint material, such as exists in patients having chondramalacia of the patella. Moreover, soft tissue, such as synovial tissue attached to the walls of the joint can be readily cut or shaped by the oscillatory action of the blade.

The means for effecting the oscillatory motion of the cutting blade comprises the heretofore mentioned stem 30 and motor 36, as well as rotary-to-oscillatory translation means 44. The means 44 basically comprises a crank element 46 and a crank arm or follower 48. The crank 46 includes a central opening 50 into which the rotary output shaft 52 of the motor 36 is located. The output shaft 52 of the motor rotates about its longitudinal central axis 54 when the motor is energized. In accordance with the preferred embodiment of the invention the motor is a pneumatic or air motor, such as sold by Micro Motors of Santa Ana, Calif. under the model designation MSM2800X. The crank 46 is fixedly mounted onto the shaft 52 via a set screw 56. A pin-like projection 58 extends from the front surface of the crank and is offset slightly laterally of the axis 54 about which the crank rotates. As can be seen clearly in FIGS. 2 and 3, the pin-like element 58 of the crank 46 is disposed within an elongated diametrically oriented slot 60 in the follower 48. The follower 48 also includes a threaded opening 62 in the front end thereof and which opening is offset laterally from one end of the slot 60 (see FIG. 3). The threaded opening 62 is arranged to receive a correspondingly threaded end 64 of the stem 30 to secure the stem to the follower. A pin 66 (FIG. 2) is provided to lock the threaded end of the stem in place in the opening 62 of the follower.

The interior of the housing 22 includes a plug 68 forming a wall located adjacent the front face of the follower 48. The wall 68 is held in place via a set screw 70. The wall 68 also includes an opening in which a bushing 72 is located. The end of the stem 30 contiguous with the threads 64 extends through the bushing 72 in the wall 68. A thrust bearing 74 is disposed at the interface between the crank 46 and the follower 48.

As will be appreciated by those skilled in the art upon the rotation of the motor's output shaft 52 about axis 54 the crank 46 rotates about that axis since the crank is secured to the shaft via set screw 56. The pin 58 of the crank 56 is located within slot 60 to couple the crank to the follower. Since the stem 30 is fixedly secured to the follower 48 at a laterally offset position and since the stem 30 is held within fixed bushing 72, the rotary action of the crank 46 about axis 54 causes the pin 58 to reciprocate with respect to slot 60, whereupon the follower 48 oscillates through a small arc about axis 32. This oscillatory motion of follower 48 is imparted to stem 30 via the fixed connection therebetween so that stem 30 also oscillates about longitudinal axis 32, through a small arc, e.g., approximately 20°-25°. Since the blade 26 is mounted on the free end of the stem, the oscillatory motion of stem 30 causes the concomitant motion of blade 26 about axis 32, whereupon the cutting edge 28 of the blade sweeps through an arc of 20°-25°.

As noted earlier, the motor 36 is secured to the rear of the housing 22. This securement is accomplished via threads 76 located at the end of the front end of the motor. An air valve 77 is mounted within the housing 22 at the opposite (rear) end of the motor and includes a valve actuator button 78 (FIG. 1). The valve includes an inlet 80 in the form of a threaded connector for securement to a line (not shown) carrying pressurized air. The valve is arranged so that upon the depression of the valve button pressurized air flows from the air line via the connector into the air motor 36. This action causes the air motor to rotate. The depression of the valve button 78 is effected by the operator (surgeon) by depressing or squeezing an actuator arm 82 mounted on the housing 22. The actuator arm is an elongated lever-like element.

With the exemplary motor described above and by the application of air pressure on the order of 50 psi, the output shaft of the motor rotates at approximately 10,000 rpm, whereupon the blade oscillates at a frequency of 166.67 Hz. By varying the air pressure to the motor, the speed of the motor, and hence the frequency of oscillation of the blade, can be controlled as desired.

In FIGS. 6, 9 and 10 the free end or tip of the sheath 38 is shown. As can be seen therein, the tip includes a slot or opening 84 centered along axis 34. The opening is of sufficient width to enable the blade 26 extending therethrough to freely oscillate without any interference of the sheath. In the exemplary tip shown in FIG. 9 the opening 84 is of generally rectangular shape with the width thereof being sufficiently wide to accommodate the full displacement or sweep of the blade 26 as it oscillates. In FIG. 10 the slot 86 through which the blade extends is of a dual flared end shape which encompasses only the area actually taken up by the blade 26 as it oscillates. As will be appreciated by those skilled in the art by making the opening that shape, one can closely configure the size of the opening to the area encompassed by the blade as it sweeps through its oscillatory motion and without providing an excess space.

As mentioned earlier the device 20 can be used with any type of cutting blade. To that end, as seen in FIG. 6 the stem 30 includes a threaded opening 88 in the end face thereof and centered on axis 32. The opening is arranged to receive the threaded end or shank 90 of a "Brimfield" type blade 26 to releasably secure it to the stem. The free end of the instrument's stem need not include the threaded opening 88, but may utilize other conventional connection means for securing other types of surgical blades thereto.

Referring now to FIGS. 2 and 5 the details of the means for effecting the extension and retraction of the shroud 38 will now be described. As mentioned earlier, the shroud basically comprises a tubular member 38 of thin walled construction. As can be seen in FIG. 2, the shroud 32 terminates in an enlarged thickness tubular wall section 92 located within the tubular front end 94 of the housing assembly 22. The section 92 includes an annular recess 96 at its front end into which the end of shroud section 38 is disposed. The section 38 and the section 92 are fixedly secured together at the interface of the annular recess 96. The section 92 extends through an opening 98 in a threaded cap 100 mounted on the end of housing section 94. The interface between the opening 98 and the shroud section 92 is of relatively low friction to enable the section 92 to reciprocate therethrough without interference. The opposite end of section 92 includes an annular recess 102 in its periphery.

As can be seen in FIG. 5, a yoke 104 having a circular recess is disposed within the annular recess 102 in the sheath section 92. The yoke includes a threaded radially extending opening 106 into which a threaded end 108 of a shaft 110 of an actuating button 112 is located. The shaft 110 of the button 112 includes an enlarged boss portion 114 including a tapered wall portion 116. A helical compression spring 118 is interposed between the yoke 104 and the boss 114. The shaft 110 of the button 112 extends through an elongated slot 120 (FIGS. 1 and 2) in the side wall of the housing portion 94. The slot 120 includes an enlarged opening 122 at the end closest to cap 100.

The extension/retraction operation of the sheath is as follows: When it is desired to insert the instrument 20 into a puncture or other small opening in the body of the patient the surgeon presses down on the top surface of instrument's pushbutton 112 and at the same time pushing forward on the button, that is toward the free end of the instrument. This action slides the button down the track 120. Inasmuch as the yoke 104 is disposed within the annular recess 102 in the sheath section 92, the movement of the button 112 down the track toward opening 122 has the effect of carrying the sheath down the stem 30 to the phantom line position denoted by the reference numeral 40 in FIG. 2. As noted earlier, in this position the blade is completely within the sheath so that its cutting blade is not exposed. The sheath is held in the extended position by virtue of the fact that when the button 112 is at the front end of track 120 its boss section 114 extends into the enlarged opening 122 under the bias of the spring 118. With the boss 14 within opening 122 the sheath is precluded from being retracted. This feature is of considerable importance to ensure that the blade is not exposed during the insertion of the instrument into the body of the patient. That insertion procedure is carried out by inserting the domed free end or tip of the shroud/stem assembly 24 into the opening in the patient and pushing forward on the instrument until the tip is located at the site where surgery is to be performed.

Once the instrument has been inserted as described above the surgeon then depresses button 112, thereby causing the button's boss portion 114 to move out of the opening 122 against the bias of spring 118. The button is then slid toward the rear of the instrument, thereby retracting the sheath, whereupon the blade 26 is fully exposed. The frictional engagement between the boss 114 and the edges of the slot 120 is sufficient to retain the sheath in the retracted position during a cutting operation.

In order to perform a resection or contouring of tissue, such as meniscal cartilage, the instrument 20 with the extended blade 26 is brought into the position so that the blade's cutting edge 28 contacts the tissue to be cut. The surgeon then depresses the actuating arm or lever 82 on the housing 22 whereupon air is provided from the valve to the motor 36 to cause the motor to operate. This action causes the blade 26 to oscillate as described heretofore. As a result of the oscillation only slight pressure is required to cut the tissue as the blade is drawn therealong. Moreover, the cutting action is quite smooth so that the tissue can be shaped or smoothed as desired. In the event that the surgeon loses sight of the cutting tip (such as by the arthroscope being aimed away from the cutting tip) the surgeon can readily extend the shroud over the blade without moving the blade from its position, thereby ensuring that no undesired cutting is accomplished.

It must be pointed out at this juncture that the choice of pneumatic power for the instrument is not exclusive. Thus, other types of motors, e.g., electric, hydraulic, etc., can be used. Moreover, the instrument of this invention need not even be powered. Thus, some manual means can be utilized to effect the oscillatory action of the blade. Further still, the shroud need not be a rigid member, but may, if desired, be formed of a somewhat flexible material, e.g., Teflon, whose blade opening may be any shape consistent with easy and safe penetration to the situs of the surgery.

Without further elaboration the foregoing will so fully illustrate our invention that others may, by applying current or future knowledge, readily adpate the same for use under various conditions of service.

I claim:

1. A surgical instrument for cutting material at a site located within the body of a patient, said instrument having a longitudinal axis for cutting said material and comprising a body portion adapted to be held, a blade having an elongated, linear cutting edge portion, cover means, and first means comprising an elongated stem member having a free end portion to which said blade is secured so that said cutting edge portion extends generally parallel to said longitudinal axis and can be fully exposed, said stem member being of small diameter to enable said blade to be inserted into said site via a small opening in the body of said patient, said cover comprising a tubular shroud disposed over said stem member and movable with respect to said cutting blade to selectively cover or expose said cutting edge portion, said first means repeatedly oscillating said blade with respect to said body portion about said longitudinal axis through a small arc and with said cutting edge portion being exposed at all times during said repeated oscillations of said blade, whereupon when said exposed cutting edge portion is brought into contact with said material and moved in a path therethrough as said blade oscillates, said cutting edge portion efficiently slices into said material.

2. The surgical instrument of claim 1 additionally comprising actuatable means coupled to said shroud for holding said shroud in either a retracted position, wherein said cutting edge portion is exposed, or an extended position, wherein said cutting edge portion is covered.

3. The surgical instrument of claim 2 wherein said actuatable means comprises a button mounted on said body portion and coupled to said shroud, said button being located within a slot in said body portion for sliding movement therein between either of two positions within said slot and including boss means cooperating with said slot to hold said button at either of said positions, whereupon said button is at one of said positions in said slot said shroud is extended and when said button is at the other of said positions in said slot said shroud is retracted.

4. The surgical of claim 3 additionally comprising spring bias means coupled to said button.

5. The surgical instrument of claim 1 wherein said instrument includes motor means for oscillating said blade.

6. The surgical instrument of claim 5 wherein said motor means comprises a rotary output shaft and wherein said surgical instrument additionally comprises translating means for translating the output of said rotary output shaft to said oscillatory movement.

7. The surgical instrument of claim 6 wherin said motor means comprises a pneumatic motor.

8. The surgical instrument of claim 6 wherein said rotary output shaft of said motor is rotatable about a central axis and wherein said translating means comprises a crank member connected to said output shaft and having a pin projecting from said crank member and offset from said central axis, said translating means also comprising a follower member having a diametrically oriented slot in which said pin is disposed, said stem member being connected to said follower member adjacent one end of said slot.

9. The surgical instrument of claim 8 wherin said cover means comprises a tubular shroud disposed over said stem member, said shroud being movable with respect to said cutting blade to selectively cover or expose said cutting edge portion.

10. The surgical instrument of claim 9 additionally comporising actuatable means coupled to said shroud for holding said shroud in either a retracted position, wherein said cutting edge portion is exposed, or an extended position, wherein said cutting edge portion is covered.

11. The surgical instrument of claim 5 wherein said body means comprises operating means for causing said motor to operate.

12. The surgical instrument of claim 11 wherein said motor is a pneumatic motor and wherein said operating means comprises depressable means and associated air valve means, said depressable means being arranged when depressed to cause said valve means to open to provide pressurized to said pneumatic motor to cause said motor to operate.

13. The device of claim 1 wherein said surgical instrument additionally comprises motor means for oscillating said blade.

14. The surgical instrument wherein said motor means comprises a rotary output shaft and wherein said surgical instrument additionally comprises translating means for translating the output of said rotary output shaft to said oscillatory movement.

15. The device of claim 14 wherein said motor means comprises a pneumatic motor.

16. The device of claim 1 wherein said arc is in the range of 15°–30°.

17. The surgical instrument of claim 1 wherein said blade is releasably secured to said stem member.

18. The surgical instrument of claim 1 wherein said shroud includes a free end having an opening through which said blade extends when said shroud is retracted.

19. The surgical instrument of claim 18 wherein said free end of said shroud is rounded.

20. The surgical instrument of claim 18 wherein said opening is closely configured to the area through which the blade sweeps as it oscillates to preclude the ingress of material into the interior of said shroud during the cutting operation.

21. The surgical instrument of claim 20 wherein said free end of said shroud is rounded.

* * * * *